United States Patent [19]
Massand

[11] Patent Number: 5,885,581
[45] Date of Patent: Mar. 23, 1999

[54] COMPOSITION AND METHOD FOR IMPROVEMENT OF THE APPEARANCE OF SCARS

[75] Inventor: Deepak Massand, McLeansville, N.C.

[73] Assignee: Merz, Incorporated, Greensboro, N.C.

[21] Appl. No.: 927,441

[22] Filed: Sep. 11, 1997

[51] Int. Cl.$^6$ .................................................... A01N 65/00
[52] U.S. Cl. ........................................................ 424/195.1
[58] Field of Search .............................. 424/195.1, 401; 514/844, 941

[56] References Cited

U.S. PATENT DOCUMENTS

| | | | |
|---|---|---|---|
| 3,876,765 | 4/1975 | Choay | 424/582 |
| 3,886,268 | 5/1975 | Halpern | 424/78.05 |
| 4,482,537 | 11/1984 | El-Menshawy et al. | 424/59 |
| 5,009,890 | 4/1991 | DiPippo | 424/195.1 |
| 5,552,162 | 9/1996 | Lee | 424/646 |

OTHER PUBLICATIONS

Lawless "The Illustrated Encyclopedia of Essential Oils," (1995) (Element Books, LTD: London) pp. 78–79, 1995.

Maragakis et al. "Possibilities of scar treatment after thoracic surgery" Drugs Under Experimental and Clinical Research (1995) 21(5): 199–206, 1995.

The Merck Index, Twelfth Edition, 255, p. 48 (1996) and 6980, p. 1174 (1996).

Marla Chadzynska et al., "Contractubex in the Treatment of Burn–Induced Hypertrophic, Keloidal Scars in Children", Der Deutsche Dermatologe 1989, 37 11: 1–4 (1989).

Published by Merz Pharma: Frankfurt (1995).

Allium cepa L.: Chemistry, Analysis and Pharmacology By: Breu, W., Dorsch, W. In: Economic and medical plant research 6: 115–147 (1994).

*Primary Examiner*—Jean C. Witz
*Assistant Examiner*—Susan Hanley
*Attorney, Agent, or Firm*—The Firm of Gordon W. Hueschen

[57] ABSTRACT

A dermatological composition for use in improving the appearance of scars comprising 20–30 parts by weight of polyethylene glycol 200, 0.005–0.03 parts by weight of preservative, 0.05–0.2 parts by weight of sorbic acid, 0.5–2 parts by weight of allantoin, 1–3 parts by weight of xanthan gum, 5–15 parts by weight of fluid onion extract (Extract Allium Cepa), dermatologically-acceptable aqueous carrier 55–65 parts by weight, perfume oil optional, for a total of 100 parts by weight, in the form of a light milky gel, and a method of improving the appearance of a scar comprising the step of applying to the scar a dermatologically-effective amount thereof.

6 Claims, No Drawings

COMPOSITION AND METHOD FOR IMPROVEMENT OF THE APPEARANCE OF SCARS

FIELD OF THE INVENTION

The present invention relates to a novel dermatological composition for use in the improvement of the appearance of scars and a method for the improvement of the appearance of scars involving employment of the said composition.

BACKGROUND OF THE INVENTION AND PRIOR ART

It is a known fact that 62 million new scars are created yearly on the skin of human beings from one cause or another, including incisions, operations, biopsies, burns, accidents, and the like, whether intentionally or unintentionally inflicted, and that present technology in the improvement of the appearance of scars has not yet provided any drug or substance of organic origin which is approved for the express purpose of improving the appearance of scars, although compositions comprising a drug to reduce erythema as by promoting decoagulation and absorption of heme or colored blood fragments, e.g., an anticoagulant such as heparin, have been proposed and although various devices including silicone sheets of the Kelocote™ type have been made available. Such silicone sheets or devices have the serious shortcoming of drying out to leave a hard and sometimes brittle, and in any event inconvenient and uncomfortably hard or stiff, sheet in the area in which applied to the skin, causing obvious discomfort to the patient, whereas dermatological compositions containing a drug of synthetic or natural origin raise questions as to overkill especially when the primary objective of the dermatological composition and method involved is cosmetic, that is, to improve the appearance of a scar. Although the individual components of the present composition have been used previously in dermatological compositions, they have not previously been combined, especially in the present proportions, and least of all in the absence of a drug serving as an active ingredient, for the present purposes.

OBJECTS OF THE INVENTION

It is an object of the present invention to provide a safe and effective dermatological composition for improving the appearance of scars and a method of improving the appearance of scars which employs the said composition. Another object of the invention is to provide such a composition which contains only safe and harmless ingredients which lack the capacity to act as drugs and which therefore have no known ulterior or side effects. A further object of the invention is to provide a simple, safe, and efficient composition for improving the appearance of scars and a method of employing the said composition for said purpose which has proven effective in practice. Other objects of the invention will become apparent hereinafter and still others will be obvious to one skilled in the art to which this invention pertains.

THE PRESENT INVENTION

The present invention comprises a light milky greaseless gel, having a pleasant fragrance depending upon whether or not a fragrance is desired in the product, which comprises polyethylene glycol 200 (PEG 4), a preservative such as methyl paraben, sorbic acid, allantoin, xanthan gum, fluid onion extract (extract Allium Cepa), purified water or other dermatologically-acceptable aqueous diluent or carrier, and fragrance to the extent desired.

When applied to scars, the composition of the present invention improves the appearance of scars by making them appear softer and smoother. Ideally, a scar is smooth, flat, and blends in with surrounding skin, but sometimes very visible and unattractive scars occur, and the composition of the present invention improves the appearance of such scars by making them blend more completely in with the surrounding skin, reducing their erythema or redness, reducing their induration or hardness, and in subjectively comforting the patient as objective symptoms decrease. This was shown to be the case in a six-month study in which substantial improvement in the appearance of scars occurred in more than 70% of the patients treated with the composition of the present invention which, for best results, should be generously applied and gently rubbed into the scar being treated three to four times daily and which may be used either on fresh scars after the wound is healed or on existing scars but which of course should not be applied to open wounds. Although nothing can make scars totally disappear or hurry the natural healing process, it is clear that the dermatological composition of the present invention is effective in improving the appearance of scars and its employment for just such purpose has been shown to be use effective.

SUMMARY OF THE INVENTION

What I believe to be my invention, then, inter alia, comprises the following, singly or in combination:

A dermatological composition for use in improving the appearance of scars comprising 20–30 parts by weight of polyethylene glycol 200, 0.005–0.03 parts by weight of preservative, 0.05–0.2 parts by weight of sorbic acid, 0.5–2 parts by weight of allantoin, 1–3 parts by weight of xanthan gum, 5–15 parts by weight of fluid onion extract (Extract Allium Cepa), dermatologically-acceptable aqueous carrier 55–65 parts by weight, perfume oil optional, for a total of 100 parts by weight, in the form of a light milky gel; such a dermatological composition comprising the following parts by weight: polyethylene glycol 200 about 25, methyl paraben about 0.015, sorbic acid about 0.1, allantoin about 1, xanthan gum about 2, fluid onion extract (Extract of Allium Cepa) about 10, purified water as the aqueous dermatologically-acceptable carrier about 61.5, perfume oil optional, for a total of 100 parts by weight, in the form of a light milky gel; and such a dermatological composition having a density at 20° C. of about 1.05–1.08 g/ml, a pH value of 4.5–5.5, and a particle size 100% of particles in the composition less than 50 $\mu$m; and a method of improving the appearance of a scar comprising the step of applying to the scar a dermatologically-effective amount of such a dermatological composition.

DETAILED DESCRIPTION OF THE INVENTION

The following examples are given to illustrate the composition and method of the present invention, but are not to be construed as limiting.

EXAMPLE 1

Generic description of the invention.

A dermatological composition or formulation is prepared from the following ingredients in the following proportions:

Polyethylene glycol 200 (PEG-4) 20 to 50% by weight
Preservative such as Methyl paraben (Nipagin M™) 0.005–0.03% by weight Sorbic acid 0.05–0.2% by weight Allantoin 0.5–2% by weight Xanthan gum (Keltrolt™) 1–3% by weight Fluid onion extract (Extract of Allium Cepa) 5–15% by weight Perfume oil (optional) 0.1–0.5% by weight Purified water or other aqueous dermatological carrier 55–65% by weight For a total of 100% by weight. The light milky gel formed by admixture of the foregoing ingredients together was packaged in tubes for use in improvement of scars by application thereto three or four times a day, the results by way of improvement in the appearance of the scars being apparent at the end of a three (3) month treatment period and significant at the end of a six (6) month treatment period.

EXAMPLE 2

Preferred specific embodiment of the invention.

The following ingredients were admixed together to form a dermatological composition in gel form:

Polyethylene glycol 200 (PEG-4) 300 kg by weight

Methyl paraben (Nipagin M™) 1.8 kg by weight

Sorbic acid 1.2 kg by weight

Allantoin 12 kg by weight

Xanthan gum (Keltrol™) 24 kg by weight

Fluid onion extract (Extract of Allium Cepa) 120 kg by weight

Perfume oil (optional) 3.6 kg by weight

Purified water as the aqueous dermatologically-acceptable carrier 737.4 kg by weight For a total of 1200 kg.

The density at 20° C. of the composition was found to be 1.05–1.06 g/ml by the Bend-Swing method, the pH value was found to be 4.5–5.5 on a standard Potentiometer, and the particle size of particles in the composition was found to be 100% smaller than 50 μm by Grindometer measurement.

The gel was filled into consumer-sized tubes and a randomly-selected portion of these tubes were employed in the clinical trials reported in Example 3 following.

EXAMPLE 3

Clinical evaluation of the composition of the present invention.

The dermatological composition of the present invention was subjected to a six-month clinical evaluation involving thirty patients having a variety of scar types using the dermatological composition of Example 2 and applying the same liberally to the scar three or four times daily. On a basis of the information collected during the course of the study, it was clear that the appearance of the scars became progressively smaller and that they became less visually apparent over the six-month period involved and that, in most cases, the changes were significantly different from baseline from four months onward. In addition, the intensity and occurrence of pain associated with the scars was reported subjectively to have been reduced by the patients and this change was significant at three months. The patients also reported that the intensity and occurrence of itching associated with the scars was reduced. At the end of the six-month treatment period, the reduction in itching intensity was statistically significant.

Substantial improvement in the appearance of the scars occurred in more than 70% of the patients in the study, and decreased redness or erythema as well as decreased induration or hardness was experienced in the majority of patients participating in the trial. There was a significant improvement in appearance of the scars treated in terms of scar length, decrease in inflammation, and decrease in induration, and there were less episodes of itching, burning, and pain by the patients participating in the trial and the intensity of these symptoms decreased. A decrease in the erythema was often, but not always, accompanied by an increase in softening, and certain types of scars were more responsive than others. Hypertrophic scars over joints showed least responsiveness, and there appeared to be a trend for older patients to show greater improvement. Surgical incision-induced hypertrophic scars were clearly the most responsive to improvement during the six-month trial. Nonetheless, substantial improvement in the appearance of the scars occurred in more than 70% of the patients participating in the trial.

Psychologically, all participants completing the trial had positive comments with regard to the improvement in the appearance of their scars and were more comfortable in view of their improved appearance.

It has accordingly been shown that a novel and effective dermatological composition for the improvement of the appearance of scars, and a method for its use for such purpose, has been provided by the present invention, and whereby all of the desirable objectives of the present invention have been attained.

It is to be understood that the present invention is not to be limited to the exact details of operation, or to the exact compounds, compositions, methods, procedures, or embodiments shown and described, as various modifications and equivalents will be apparent to one skilled in the art, wherefore the present invention is to be limited only by the full scope which can be legally accorded to the appended claims.

I claim:

1. A dermatological composition for use in improving the appearance of scars consisting essentially of 20–30 parts by weight of polyethylene glycol 200, 0.005–0.03 parts by weight of preservative, 0.05–0.2 parts by weight of sorbic acid, 0.5–2 parts by weight of allantoin, 1–3 parts by weight of xanthan gum, 5–15 parts by weight of fluid onion extract (Extract Allium Cepa), and a dermatologically-acceptable aqueous carrier 55–65 parts by weight, for a total of 100 parts by weight, in the form of a milky gel.

2. The dermatological composition of claim 1 consisting essentially of the following parts by weight: polyethylene glycol 200 about 25, methyl paraben about 0.015, sorbic acid about 0.1, allantoin about 1, xanthan gum about 2, fluid onion extract (Extract of Allium Cepa) about 10; and purified water as the aqueous dermatologically-acceptable carrier about 61.5, for a total of 100 parts by weight, in the form of a milky gel.

3. The dermatological composition of claim 2 wherein said composition have a density at 20° C. of about 1.05–1.08 g/ml, a pH value of 4.5–55; and particles, wherein 100% of said particles have a size of less than 50 μm.

4. A method of improving the appearance of a scar consisting essentially of the step of applying to the scar a dermatologically-effective amount of a composition of claim 1.

5. A method of improving the appearance of a scar consisting essentially of the step of applying to the scar a dermatologically-effective amount of a composition of claim 2.

6. A method of improving the appearance of a scar consisting essentially of the step of applying to the scar a dermatologically-effective amount of a composition of claim 3.

* * * * *

UNITED STATES PATENT AND TRADEMARK OFFICE
CERTIFICATE OF CORRECTION

PATENT NO. : 5,885,581
DATED : March 23, 1999
INVENTOR(S) : Deepak Massand It is certified that error appears in the above-identified patent and that said Letters Patent is hereby corrected as shown below:

Title Page, OTHER PUBLICATIONS, Column 2, 3rd item: "Published by Merz Pharma: Frankfurt (1995).", in front of this please <u>insert</u>: -- Contractubex Specific: treatment for scars, Scientific Information booklet by The Clinical Research Department of Merz + Co. GmbH & Co., Cover and pages 1-28. --.

Column 4, line 51: "have" should read -- has --.

Signed and Sealed this

Ninth Day of November, 1999

Q. TODD DICKINSON

*Attest:*

*Attesting Officer*  *Acting Commissioner of Patents and Trademarks*